US012651345B2

(12) United States Patent
Shao et al.

(10) Patent No.: US 12,651,345 B2
(45) Date of Patent: Jun. 9, 2026

(54) SYSTEM AND METHOD FOR REGION STRATIFICATION ON CALIBRATION IMAGES

(71) Applicant: GE Precision Healthcare LLC, Waukesha, WI (US)

(72) Inventors: Muhan Shao, Clifton Park, NY (US); Chitresh Bhushan, Glenville, NY (US); Dattesh Dayanand Shanbhag, Bangalore (IN); Kavitha Manickam, Pewaukee, WI (US); Dawei Gui, Sussex, WI (US)

(73) Assignee: GE Precision Healthcare LLC, Waukesha, WI (US)

( * ) Notice: Subject to any disclaimer, the term of this patent is extended or adjusted under 35 U.S.C. 154(b) by 301 days.

(21) Appl. No.: 18/491,985

(22) Filed: Oct. 23, 2023

(65) Prior Publication Data

US 2025/0131570 A1     Apr. 24, 2025

(51) Int. Cl.
| | |
|---|---|
| *G06T 7/11* | (2017.01) |
| *G01R 33/48* | (2006.01) |
| *G01R 33/56* | (2006.01) |
| *G01R 33/58* | (2006.01) |
| *G06T 7/73* | (2017.01) |

(Continued)

(52) U.S. Cl.
CPC .............. *G06T 7/11* (2017.01); *G01R 33/481* (2013.01); *G01R 33/5608* (2013.01); *G01R 33/583* (2013.01); *G06T 7/73* (2017.01); *G06V 10/82* (2022.01); *G06V 20/50* (2022.01); *G06V 20/70* (2022.01); *G16H 30/40* (2018.01); *A61B 5/055* (2013.01); *G06T*

*2207/10088* (2013.01); *G06T 2207/10104* (2013.01); *G06T 2207/20021* (2013.01); *G06T 2207/20081* (2013.01);

(Continued)

(58) Field of Classification Search
None
See application file for complete search history.

(56) References Cited

U.S. PATENT DOCUMENTS

| | | |
|---|---|---|
| 11,506,739 B2 | 11/2022 | Gui et al. |
| 2019/0369180 A1* | 12/2019 | Chang .................. G01R 33/443 |

(Continued)

FOREIGN PATENT DOCUMENTS

| | | | |
|---|---|---|---|
| WO | WO-2022056501 A1* | 3/2022 | ........... G01R 33/481 |

*Primary Examiner* — Bernard Krasnic
(74) *Attorney, Agent, or Firm* — Fletcher Yoder, P.C.

(57) ABSTRACT

A method and a system include obtaining calibration scan data or low resolution images of a subject acquired with a magnetic resonance (MR) scanner of an MR imaging system. The method and the system also include inputting the calibration data or the low resolution images into a trained deep learning-based multi-mask segmentation network. The method and the system further include outputting labeled mask images for different anatomical stations, wherein a respective mask of a respective labeled mask image highlights an anatomical landmark of interest in each respective anatomical station of the different anatomical stations. The method and the system even further include determining an extent of a respective anatomical landmark of interest in each respective anatomical station of the different anatomical stations for a respective localizer scan for each respective anatomical station based at least on a respective label mask image for each respective anatomical station.

13 Claims, 9 Drawing Sheets

(51) Int. Cl.

| | | |
|---|---|---|
| *G06V 10/82* | (2022.01) | |
| *G06V 20/50* | (2022.01) | |
| *G06V 20/70* | (2022.01) | |
| *G16H 30/40* | (2018.01) | |
| *A61B 5/055* | (2006.01) | |

(52) U.S. Cl.
    CPC .............. *G06T 2207/20084* (2013.01); *G06T 2207/30012* (2013.01); *G06V 2201/033* (2022.01)

(56)                    References Cited

U.S. PATENT DOCUMENTS

| | | | |
|---|---|---|---|
| 2019/0369198 A1* | 12/2019 | Chang ................ | G01R 33/3664 |
| 2021/0080531 A1* | 3/2021 | Gui ........................ | G01R 33/58 |
| 2021/0244328 A1* | 8/2021 | Kates-Harbeck ...... | A61B 5/245 |

* cited by examiner

180     → • Spine Multi-Mask Segmentation Network

182     → • Whole Body Multi-Mask Segmentation Network

184     → • PET/MR MRAC Multi-Mask Segmentation Network

186     → • ROI Multi-Mask Segmentation Network

—240

—246

—248

SYSTEM AND METHOD FOR REGION STRATIFICATION ON CALIBRATION IMAGES

BACKGROUND

The subject matter disclosed herein relates to medical imaging and, more particularly, to a system and a method for region stratification on calibration images.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

During magnetic resonance imaging (MRI), when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment, Mt. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradient fields vary according to the particular localization method being used. The resulting set of received nuclear magnetic resonance (NMR) signals are digitized and processed to reconstruct the image using one of many well-known reconstruction techniques.

Whole body scanning (e.g., of the head, spine, abdomen, pelvis, and heart) in MRI enables MRI of the entire body to be performed in a single imaging session. However, whole body scanning in MRI is not straightforward due to multiple stations (e.g., anatomic stations) or anatomy stratification which is needed on multiple localizer images. Similarly, spine scanning with MRI is cumbersome due to multiple stations being involved and having to find the extents of cervical, lumbar, and thoracic regions. Accordingly, a technologist has to acquire multiple localizers and then work across the multiple set of localizers to determine the boundaries across stations and to scan to obtain higher resolution images. This may also involve additional processing with regard to image cropping, image pasting (e.g., digital stitching of image segments together), and other processing techniques.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a computer-implemented method for performing region stratification on calibration images or low resolution images is provided. The computer-implemented method includes obtaining, at a processor, calibration scan data or low resolution images of a subject acquired with a magnetic resonance (MR) scanner of an MR imaging system. The computer-implemented method also includes inputting, via the processor, the calibration data or the low resolution image into a trained deep learning-based multi-mask segmentation network. The computer-implemented method further includes outputting, via the processor, labeled mask images for different anatomical stations, wherein a respective mask of a respective labeled mask image highlights an anatomical landmark of interest in each respective anatomical station of the different anatomical stations. The computer-implemented method even further includes determining, via the processor, an extent of a respective anatomical landmark of interest in each respective anatomical station of the different anatomical stations for a respective localizer scan for each respective anatomical station based at least on a respective label mask image for each respective anatomical station In another embodiment, a system for performing region stratification on calibration images or low resolution images is provided. The system includes a memory encoding processor-executable routines. The system also includes a processor configured to access the memory and to execute the processor-executable routines, wherein the routines, when executed by the processor, cause the processor to perform actions. The actions include obtaining calibration scan data or low resolution images of a subject acquired with a magnetic resonance (MR) scanner of an MR imaging system. The actions also include inputting the calibration data or the low resolution images into a trained deep learning-based multi-mask segmentation network. The actions further include outputting labeled mask images for different anatomical stations, wherein a respective mask of a respective labeled mask image highlights an anatomical landmark of interest in each respective anatomical station of the different anatomical stations. The actions even further include determining an extent of a respective anatomical landmark of interest in each respective anatomical station of the different anatomical stations for a respective localizer scan for each respective anatomical station based at least on a respective label mask image for each respective anatomical station.

In a further embodiment, a non-transitory computer-readable medium, the computer-readable medium including processor-executable code that when executed by a processor, causes the processor to perform actions. The actions include obtaining calibration scan data or low resolution images of the subject acquired with a magnetic resonance (MR) scanner of an MR imaging system. The actions also include inputting the calibration data or the low resolution image into a trained deep learning-based multi-mask segmentation network. The actions further include outputting labeled mask images for different anatomical stations, wherein a respective mask of a respective labeled mask image highlights an anatomical landmark of interest in each respective anatomical station of the different anatomical stations. The actions even further include determining an extent of a respective anatomical landmark of interest in each respective anatomical station of the different anatomical stations for a respective localizer scan for each respective anatomical station based at least on a respective label mask image for each respective anatomical station.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
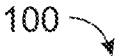
FIG. 1 illustrates a schematic diagram of a magnetic resonance imaging (MRI) system suitable for use with the disclosed techniques.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

Deep learning (DL) approaches discussed herein may be based on artificial neural networks, and may therefore encompass one or more of deep neural networks, fully connected networks, convolutional neural networks (CNNs), unrolled neural networks, perceptrons, encoders-decoders, recurrent networks, wavelet filter banks, u-nets, general adversarial networks (GANs), dense neural networks, or other neural network architectures. The neural networks may include shortcuts, activations, batch-normalization layers, and/or other features. These techniques are referred to herein as DL techniques, though this terminology may also be used specifically in reference to the use of deep neural networks, which is a neural network having a plurality of layers.

As discussed herein, DL techniques (which may also be known as deep machine learning, hierarchical learning, or deep structured learning) are a branch of machine learning techniques that employ mathematical representations of data and artificial neural networks for learning and processing such representations. By way of example, DL approaches may be characterized by their use of one or more algorithms to extract or model high level abstractions of a type of data-of-interest. This may be accomplished using one or more processing layers, with each layer typically corresponding to a different level of abstraction and, therefore, potentially employing or utilizing different aspects of the initial data or outputs of a preceding layer (i.e., a hierarchy or cascade of layers) as the target of the processes or algorithms of a given layer. In an image processing or reconstruction context, this may be characterized as different layers corresponding to the different feature levels or resolution in the data. In general, the processing from one representation space to the next-level representation space can be considered as one 'stage' of the process. Each stage of the process can be performed by separate neural networks or by different parts of one larger neural network.

The present disclosure provides systems and methods for performing region stratification on calibration images. In particular, the systems and the methods obtaining coil calibration scan data (e.g., coil calibration images) of the subject acquired during a prescan with a magnetic resonance (MR) scanner of an MR imaging system. The methods and the systems also include inputting the coil calibration data into a trained deep learning-based multi-mask segmentation network. The methods and the systems further include outputting labeled mask images for different anatomical stations (or regions marked with boundaries), wherein a respective mask of a respective labeled mask image highlights an anatomical landmark of interest in each respective anatomical station of the different anatomical stations. In certain embodiments, more than one anatomical landmark of interest maybe labeled in a particular anatomical station. Also, a mask may be a point landmark or multi-point station delineating region. The methods and the systems even further include determining an extent of a respective anatomical landmark of interest in each respective anatomical station of the different anatomical stations for a respective localizer scan for each respective anatomical station based at least on a respective label mask image for each respective anatomical station.

In certain embodiments, the described systems and methods may be utilized on low resolution images (as opposed to calibration images). Low resolution images are non-diagnostic images having a lower resolution than a diagnostic image. In certain embodiments, the described systems and methods may be utilized on calibration data other than coil calibration data (e.g., ASSET/PURE calibration). In certain embodiments, the calibration data may be obtained from prescan calibration or task calibration. The calibration data may be raw or processed.

The deep learning-based multi-mask segmentation network is trained to detect and to label the respective anatomical landmark of interest in each respective anatomical station of the different anatomical stations. In certain embodiments, the systems and the methods yet further include obtaining requirements for the scan of the subject (e.g., scan protocol, region of interest to be scanned, purpose of the scan, etc.). In certain embodiments, determining the extent of the respective anatomical landmark of interest in each respective anatomical station of the different anatomical stations for the respective localizer scan for each respective anatomical station based on both the respective label mask image for each respective anatomical station and the requirements for the scan of the subject. In certain embodiments, the coil calibration scan data is obtained from a single radio frequency coil. In certain embodiments, the coil calibration data is obtained from a plurality of radio frequency coils. The calibration data may be raw or processed. The radio frequency coils may include single channel or multi-channel radio frequency body or surface or transmit/receive or receive only coils. In certain embodiments, the extent of the respective anatomical landmark of interest in each respective anatomical station of the different anatomical stations is determined for each radio frequency coil of the plurality of radio frequency coils for the respective localizer scan for each respective anatomical station. In certain embodiments, the different anatomical stations are for a spine scan with the MR scanner. In certain embodiments, the different anatomical stations are for a whole body scan with the MR scanner. In certain embodiments, the different anatomical stations are for an MRI-based attenuation correction (MRAC) scan with the MR scanner and a positron emission tomography (PET) scanner, wherein the MR imaging system is part of a PET/MR imaging system.

The disclosed embodiments provide for automatic patient specific extent estimation for correct localizer or high resolution scans during a prescan stage. For example, the disclosed embodiments enable techniques to determine a spine station (e.g., cervical, thoracic, lumbar) extent automatically from calibration images as part of a prescan and have the correct station localizer scanned for further usage by the technologist in planning a spine examination. These techniques can be extended to determining other anatomical boundaries in context of a whole body imaging or PET/MR MRAC boundaries. With these techniques, all the presets necessary for region stratification are made available from prescan data and geometrically with geometrically and patient specific localizers made available on the go for the technologist. This ensures that the correct station (e.g., cervical only or thoracic only or lumbar only) or station (e.g., cervico-throracic, thoraco-lumbar or entire spine) localizers are automatically available to a user for spine planning. This is especially so for the thoracic station, which is typically split across two localizers in current practice. This approach allows for a single localizer to be generated automatically and removes the need for pasting and facilitates easy setup for planning the examination. The disclosed embodiments are also useful for automatically setting up the patient anatomy specific superior/inferior coverage preset for multi-station whole body imaging examination (e.g., PET/MR MRAC). The disclosed embodiments further reduce the time in setting up a subsequent can (e.g., localizer scan and/or higher resolution scan (e.g., diagnostic scan)).

Although the techniques described below are utilized with an MRI system, in certain embodiments, the techniques may be utilized with a PET/MR imaging system. For example, the techniques described below may be utilized for a PET/MR MRAC scan.

With the preceding in mind, FIG. 1 a magnetic resonance imaging (MRI) system 100 is illustrated schematically as including a scanner 102, scanner control circuitry 104, and system control circuitry 106. According to the embodiments described herein, the MRI system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 (e.g., subject) to be positioned therein for imaging selected anatomy within the patient.

Scanner 102 includes a series of associated coils for producing controlled magnetic fields for exciting the gyromagnetic material within the anatomy of the patient being imaged. Specifically, a primary magnet coil 128 is provided for generating a primary magnetic field, $B_0$, which is generally aligned with the bore 122. A series of gradient coils 130, 132, and 134 permit controlled magnetic gradient fields to be generated for positional encoding of certain gyromagnetic nuclei within the patient 126 during examination sequences. A radio frequency (RF) coil 136 (e.g., RF transmit coil) is configured to generate radio frequency pulses for exciting the certain gyromagnetic nuclei within the patient.

In addition to the coils that may be local to the scanner 102, the system 100 also includes a set of receiving coils or RF receiving coils 138 (e.g., an array of coils) configured for placement proximal (e.g., against) to the patient 126. As an example, the receiving coils 138 can include cervical/tho-racic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, $B_0$. A power input (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuitry 104.

Another control circuit 152 is provided for regulating operation of the RF coil 136. Circuit 152 includes a switch-ing device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals pro-duced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illus-trated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitiz-ers, and processors may be disposed between the scanner and either or both of the scanner and system control circuitry 104, 106.

As illustrated, scanner control circuitry 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent pro-cessing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuitry 104 and system control circuitry 106. In certain embodiments, the control and analysis circuit 160, while illustrated as a single unit, may include one or more hard-ware devices. The system control circuit 106 includes an interface circuit 166, which receives data from the scanner control circuitry 104 and transmits data and commands back to the scanner control circuitry 104. The control and analysis circuit 168 may include a CPU in a multi-purpose or application specific computer or workstation. Control and analysis circuit 168 is coupled to a memory circuit 170 to store programming code for operation of the MRI system 100 and to store the processed image data for later recon-struction, display and transmission. The programming code may execute one or more algorithms that, when executed by a processor, are configured to perform reconstruction of acquired data as described below. In certain embodiments, the memory circuit 170 may store one or more neural networks (e.g., deep learning-based multi-mask segmenta-tion network for a spine scan, deep learning-based multi-mask segmentation network for a whole body scan, deep learning-based multi-mask segmentation network for PET/MR MRAC scan, deep learning-based multi-mask segmen-tation network for region of interest, etc.) for performing region stratification on calibration images as described below. In certain embodiments, image reconstruction may occur on a separate computing device having processing circuitry and memory circuitry.

The programming code may enable for performing region stratification on calibration images. In particular, the pro-gramming code may also enable obtaining coil calibration scan data (e.g., coil calibration images) of the subject acquired during a prescan with a magnetic resonance (MR) scanner of an MR imaging system. The programming code may also enable inputting the coil calibration data into a trained deep learning-based multi-mask segmentation net-work. The calibration data may be raw or processed. The programming code may also enable outputting labeled mask images for different anatomical stations, wherein a respec-tive mask of a respective labeled mask image highlights an anatomical landmark of interest in each respective anatomi-cal station of the different anatomical stations. A mask may be a point landmark or multi-point station delineating region. The programming code may also enable determining an extent of a respective anatomical landmark of interest in each respective anatomical station of the different anatomi-cal stations for a respective localizer scan for each respective anatomical station based at least on a respective label mask image for each respective anatomical station.

The deep learning-based multi-mask segmentation net-work is trained to detect and to label the respective ana-tomical landmark of interest in each respective anatomical station of the different anatomical stations. In certain embodiments, the programming code may also enable obtaining requirements for the scan of the subject (e.g., scan protocol, region of interest to be scanned, purpose of the scan, etc.). In certain embodiments, determining the extent of the respective anatomical landmark of interest in each respective anatomical station of the different anatomical stations for the respective localizer scan for each respective anatomical station based on both the respective label mask image for each respective anatomical station and the require-ments for the scan of the subject. In certain embodiments, the coil calibration scan data is obtained from a single radio frequency coil. In certain embodiments, the coil calibration data is obtained from a plurality of radio frequency coils. The calibration data may be raw or processed. The radio frequency coils may include single channel or multi-channel radio frequency body or surface or transmit/receive or receive only coils. In certain embodiments, the extent of the respective anatomical landmark of interest in each respective anatomical station of the different anatomical stations is determined for each radio frequency coil of the plurality of radio frequency coils for the respective localizer scan for each respective anatomical station. In certain embodiments, the different anatomical stations are for a spine scan with the MR scanner. In certain embodiments, the different anatomical stations are for a whole body scan with the MR scanner. In certain embodiments, the different anatomical stations are for a PET/MR MRAC scan with the MR scanner and a positron emission tomography (PET) scanner, wherein the MR imaging system is part of a PET/MR imaging system.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

Figure 2:
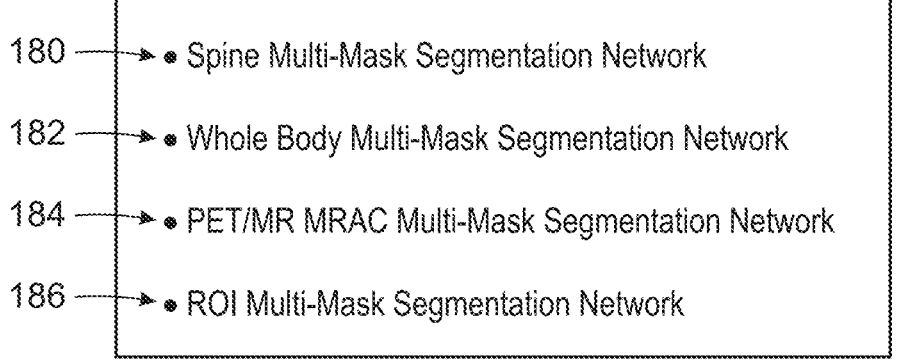
FIG. 2 is a schematic diagram illustrating examples of deep learning-based multi-mask segmentation networks, in accordance with aspects of the present disclosure.

FIG. 2 is a schematic diagram illustrating examples of deep learning-based multi-mask segmentation networks. Each deep learning-based multi-mask segmentation network is trained via supervised learning on input-output data pairs. Each deep learning-based multi-mask segmentation network is configured to receive an input of coil calibration data (e.g., coil calibration images). In certain embodiments, the coil calibration data is obtained during a prescan from a single coil (e.g., surface RF coil or body RF coil). In certain embodiments, the coil calibration data is obtained during a prescan from multiple coils (e.g., surface RF coil and body RF coil). The calibration data may be raw or processed. The radio frequency coils may include single channel or multi-channel radio frequency body or surface or transmit/receive or receive only coils. Each deep learning-based multi-mask segmentation network is also configured to output labeled mask images for different anatomical stations, wherein a respective mask of a respective labeled mask image highlights an anatomical landmark of interest in each respective anatomical station of different anatomical stations. In particular, each deep learning-based multi-mask segmentation network is trained to detect and to label a respective anatomical landmark of interest in each respective anatomical station of the different anatomical stations. A mask may be a point landmark or multi-point station delineating region.

Figure 3:
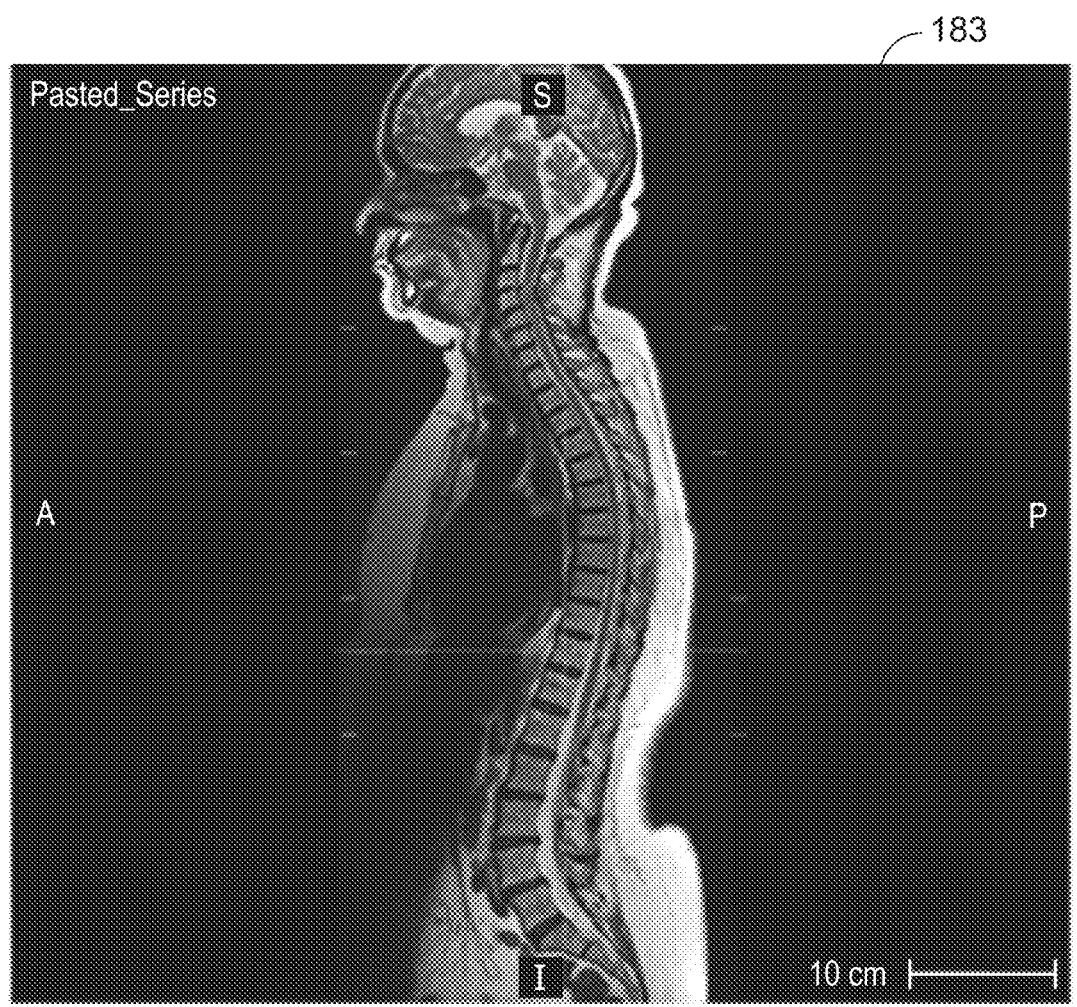
FIG. 3 is an example of an MR image including an entire spine, in accordance with aspects of the present disclosure.

As depicted in FIG. 2, a deep learning-based spine multi-mask segmentation network 180 is trained for utilization with a spine scan. In particular, the deep learning-based spine multi-mask segmentation network 180 is configured to detect and to label the cervical portion of the spine, the thoracic portion of the spine, and the lumbar portion of the spine for the cervical spine station, the thoracic spine station, and the lumbar spine station, respectively. In certain embodiments, the deep learning-based spine multi-mask segmentation network 180 is configured to detect and to label both the cervical and thoracic portion of the spine for a cervico-thoracic spine station, to detect and to label both a thoracic portion and a lumbar portion of a spine for a thoraco-lumbar spine station, and/or to detect and to label an entirety of a spine for a spine station. FIG. 3 is an example of an MR image 183 including an entire spine. The MR image 183 is along a sagittal plane. The MR image 183 has been generated via pasting (e.g., digital stitching or merging of image segments together) of different images from a scanning session of subject. The MR image 183 may be utilized as a ground truth in training the deep learning-based spine multi-mask segmentation network 180.

As depicted in FIG. 2, a deep learning-based whole body multi-mask segmentation network 182 is trained for utilization with a whole body scan. In particular, the deep learning-based whole body multi-mask segmentation network 182 is configured to detect and to label different regions of the body along the superior-inferior direction. The number of anatomical stations and what anatomical landmarks are of interest in each anatomical station may vary depending on the scan protocol. In one example, the anatomical stations may be for the head, the thorax, the abdomen, and the pelvis region. In certain embodiments, the deep learning-based whole body multi-mask segmentation network 182 may be configured to detect and to label different regions of the body along other directions (e.g., right-left direction or anterior-posterior directions).

As depicted in FIG. 2, a deep learning-based PET/MR MRAC multi-mask segmentation network 184 is trained for utilization with a PET/MR MRAC scan. In particular, the deep learning-based PET/MR MRAC multi-mask segmentation network 184 is configured to detect and to label different regions of the body along the superior-anterior direction. The number of anatomical stations and what anatomical landmarks are of interest in each anatomical station may vary depending on the scan protocol. In one example, the anatomical stations may be for the head, the thorax, the abdomen, and the pelvis region.

As depicted in FIG. 2, a deep learning-based region of interest (ROI) multi-mask segmentation network 186 is trained for utilization with a scan of a region of interest. In particular, the deep learning-based region of interest multi-mask segmentation network 186 is configured to detect and to label different anatomical landmarks in a region of interest. For example, the deep learning-based region of interest multi-mask segmentation network 186 may be for different parts of a lung. In another example, the deep learning-based region of interest multi-mask segmentation network 186 may be for different parts of a shoulder or another region of interest.

In certain embodiments, the memory circuitry of an MRI system (e.g., MRI system 100 in FIG. 1) or of a remote computing device may include only one of the deep learning-based spine multi-mask segmentation network 180, the deep learning-based whole body multi-mask segmentation network 182, the deep learning-based PET/MR MRAC multi-mask segmentation network 184, and the deep learning-based region of interest multi-mask segmentation network 186 for utilization by the processing circuitry. In certain embodiments, the memory circuitry of an MRI system (e.g., MRI system 100 in FIG. 1) or of a remote computing device may include two or more of the deep learning-based spine multi-mask segmentation network 180, the deep learning-based whole body multi-mask segmentation network 182, the deep learning-based PET/MR MRAC multi-mask segmentation network 184, and the deep learning-based region of interest multi-mask segmentation network 186 for utilization by the processing circuitry.

Figure 4:
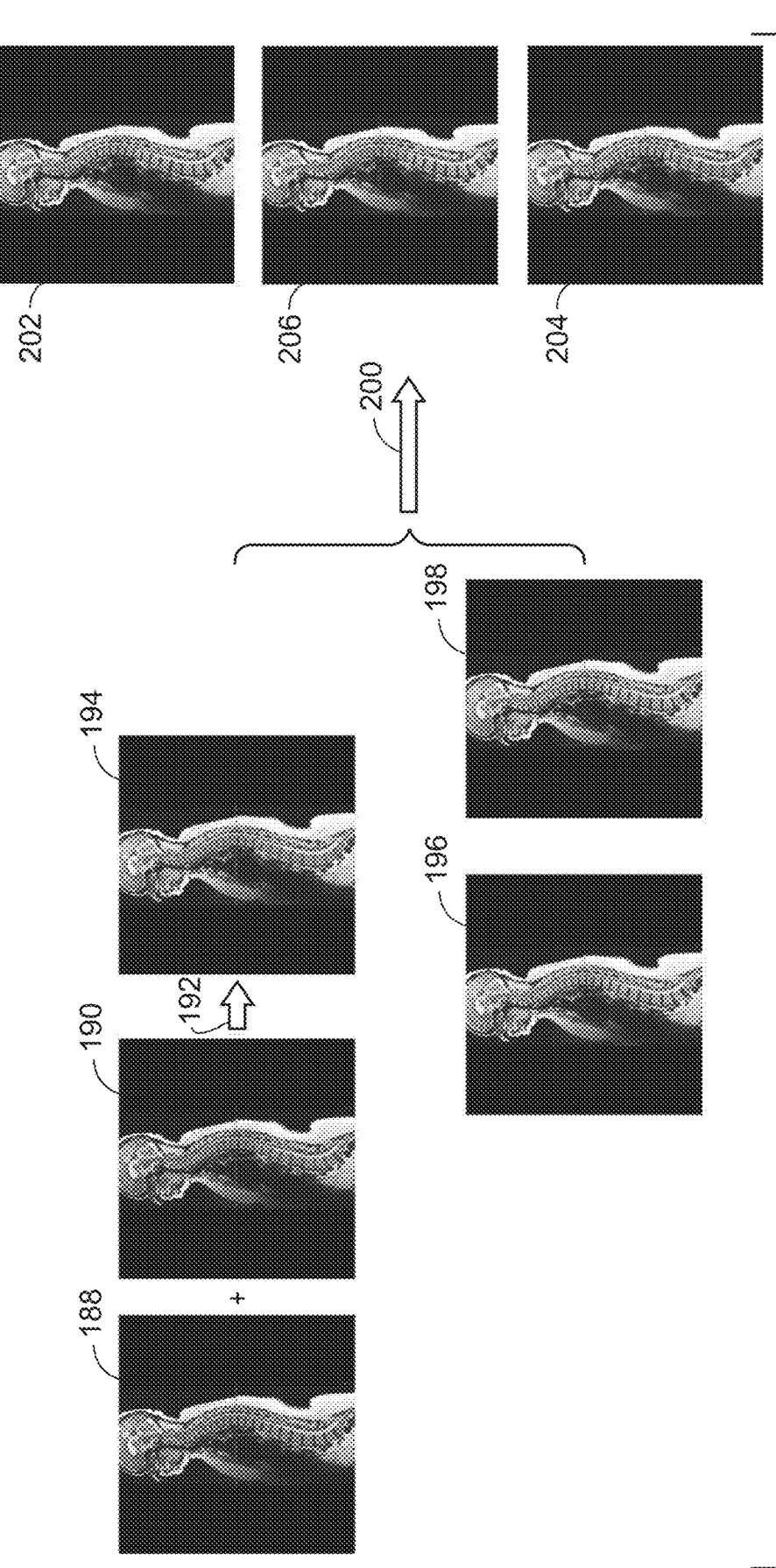
FIG. 4 is a schematic diagram illustrating how to create ground truths for labeling multiple stations for a spine scan, in accordance with aspects of the present disclosure.

FIG. 4 is a schematic diagram illustrating how to create ground truths for labeling multiple stations for a spine scan. As depicted in FIG. 4, a vertebrae segmentation mask image 188 is generated. The vertebrae segmentation mask image 188 is generated by utilizing a deep learning-based model trained for segmenting vertebrae on an MR image (along a sagittal plane) of pasted data that includes an entirety of a spine. As depicted in the vertebrae segmentation mask image 188, all of the vertebrae of the spine are labeled (e.g., highlighted) with a segmentation mask.

In addition, as depicted in FIG. 4, a disc segmentation mask image 190 is generated. The disc segmentation mask image 190 is generated by utilizing a deep learning-based model trained for segmenting discs on an MR image (along a sagittal plane) of pasted data that includes an entirety of a spine. As depicted in the disc segmentation mask image 190, all of the discs of the spine are labeled (e.g., highlighted) with a segmentation mask.

Further, as depicted in FIG. 4, the vertebrate segmentation mask image 188 is combined (as indicated by arrow 192) with the disc segmentation mask image 190 to generate a combined spine segmentation mask image 194. As depicted in the combined spine segmentation mask image 194, all the vertebrae and discs are labeled (e.g., highlighted) with a segmentation mask.

Even further, as depicted in FIG. 4, a cervical segmentation mask image 196 is generated. The cervical segmentation mask image 196 is generated by utilizing a deep learning-based model trained for segmenting cervical vertebrae on an MR image (along a sagittal plane) of pasted data that includes an entirety of a spine. As depicted in the cervical segmentation mask image 196, all of the cervical vertebrae of the spine are labeled (e.g., highlighted) with a segmentation mask.

Yet further, as depicted in FIG. 4, a lumbar segmentation mask image 198 is generated. The lumbar segmentation mask image 198 is generated by utilizing a deep learning-based model trained for segmenting lumbar vertebrae on an MR image (along a sagittal plane) of pasted data that includes an entirety of a spine. As depicted in the lumbar segmentation mask image 198, all of the lumbar vertebrae of the spine are labeled (e.g., highlighted) with a segmentation mask.

As depicted in FIG. 4, as indicated by arrow 200, the cervical segmentation mask image 196 and the lumbar segmentation mask image 198 are utilized to separate the combined spine segmentation mask image 194 to generate both a cervical segmentation mask image 202 and a lumbar mask segmentation image 204. In the cervical segmentation mask image 202, both the cervical vertebrae and the discs between the cervical vertebrae are labeled (e.g., highlighted) with a segmentation mask. In the lumbar mask segmentation mask image 204, both the lumbar vertebrae and the discs between the lumbar vertebrae are labeled (e.g., highlighted) with a segmentation mask. The remaining part results in the generation of a thoracic segmentation mask image 206. In the thoracic segmentation mask image 208, both the thoracic vertebrae and the discs between the thoracic vertebrae are labeled (e.g., highlighted) with a segmentation mask.

The cervical segmentation mask image 202, the lumbar segmentation mask image 204, and the thoracic segmentation mask image 208 can be utilized as ground truths in training a deep learning-based spine multi-mask segmentation network to detect and to label the cervical portion of the spine, the thoracic portion of the spine, and the lumbar portion of the spine for the cervical spine station, the thoracic spine station, and the lumbar spine station, respectively. In certain embodiments, the cervical segmentation mask image 202, the lumbar segmentation mask image 204, and the thoracic segmentation mask image 208 can be utilized as ground truths in training a deep learning-based spine multi-mask segmentation network to detect and to label both the cervical and thoracic portion of the spine for a cervico-thoracic spine station, to detect and to label both a thoracic portion and a lumbar portion of a spine for a thoraco-lumbar spine station, and/or to detect and to label an entirety of a spine for a spine station.

Figure 5:
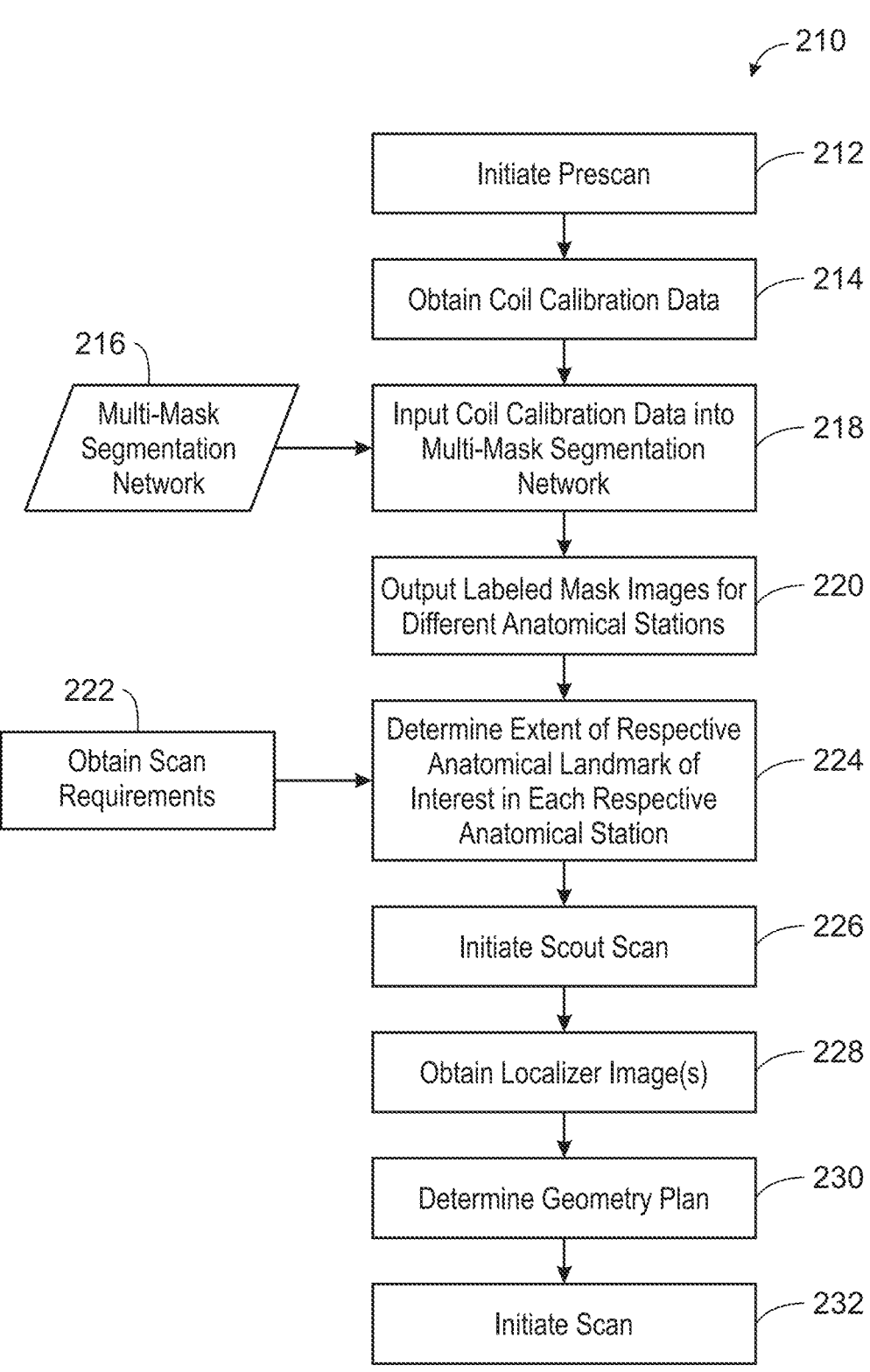
FIG. 5 illustrates a flow diagram of a method for performing a scan of a patient utilizing the MRI system in FIG. 1, in accordance with aspects of the present disclosure.

FIG. 5 illustrates a flow diagram of a method 210 for performing a scan of a patient utilizing the MRI system 100 in FIG. 1. One or more steps of the method 210 may be performed by processing circuitry of the magnetic resonance imaging system 100 in FIG. 1. One or more of the steps of the method 210 may be performed simultaneously or in a different order from the order depicted in FIG. 5. In certain embodiments, the method 210 may be utilized on low resolution images (as opposed to calibration images). Low resolution images are non-diagnostic images having a lower resolution than a diagnostic image. In certain embodiments, the method 210 may be utilized on calibration data other than coil calibration data (e.g., ASSET/PURE calibration). In certain embodiments, the calibration data may be obtained from prescan calibration or task calibration. The calibration data may be raw or processed.

The method 210 includes initiating a prescan of a subject with an MR scanner (e.g., MR scanner 102) in FIG. 1 (block 212). The prescan include performing a coil calibration scan utilizing one or more coils (e.g., RF surface coil and/or RF body coil).

The method 210 also includes obtaining coil calibration scan data (e.g. coil calibration images) of the subject acquired during the prescan with the MR scanner (block 214). The coil calibration data is large field of view coil calibration data. The method 210 further includes inputting the coil calibration data into a trained deep learning-based multi-mask segmentation network 216 (block 218). In certain embodiments, the deep learning-based multi-mask segmentation network is trained for a spine scan. In certain embodiments, the deep learning-based multi-mask segmentation network is trained for a whole body scan. In certain embodiments, the deep learning-based multi-mask segmentation network 216 is trained for a PET/MR MRAC scan. In certain embodiments, the deep learning-based multi-mask segmentation network 216 is trained for a non-PET/MR whole body planning workflow. In certain embodiments, the deep learning-based segmentation network 216 is trained for a scan of a different and specific region of interest (e.g., lung, shoulder, etc.). The deep learning-based multi-mask segmentation network is trained to detect and to label a respective anatomical landmark of interest in each respective anatomical station of the different anatomical stations.

The method 210 further includes outputting labeled mask images for different anatomical stations, wherein a respective mask of a respective labeled mask image highlights an anatomical landmark of interest in each respective anatomical station of the different anatomical stations (block 220). In certain embodiments, more than one anatomical landmark of interest maybe labeled in a particular anatomical station. The method 210 yet further includes obtaining requirements or information for a scan of the subject (e.g., subsequent scan such as a localizer scan or a diagnostic scan) (block 222). The requirements or information may include a scan protocol, region of interest to be scanned, purpose of the scan, or other information. The requirements or information may be obtained from electronic medical records, radiology information system, and/or other source.

The method 210 even further includes determining (e.g., automatically) an extent (e.g., appropriate field of view (which is superior/inferior based)) of a respective anatomical landmark of interest in each respective anatomical station of the different anatomical stations for a respective localizer scan for each respective anatomical station based at least on a respective label mask image for each respective anatomical station (block 224). In certain embodiments, determining the extent of the respective anatomical landmark of interest in each respective anatomical station of the different anatomical stations for the respective localizer scan for each respective anatomical station based on both the respective label mask image for each respective anatomical station and the requirements for the scan of the subject. In certain embodiments (when the coil calibration data is obtained from a single RF coil), the extents are determined for the respective anatomical landmark of interest in each respective anatomical station of the different anatomical stations for the single RF coil. In certain embodiments (when the coil calibration data is obtained from multiple RF coils), the extents are determined for the respective anatomical landmark of interest in each respective anatomical station of the different anatomical stations for each of the multiple RF coils.

The method 210 further includes initiating a scout scan (e.g., non-diagnostic scan) of the subject with the MRI system to obtain respective localizer or scout images for one or more of the different anatomical stations based on the determined extents of the respective anatomical landmarks of interest (block 226). The localizer images are a series of images (e.g., two-dimensional (2D) images) in the axial, sagittal, and coronal planes (e.g., 3-plane localizer scans). The method 210 even further includes obtaining the localizer images including an anatomic landmark of interest of the subject for one or more of the different anatomical stations (block 228). The method 210 still further includes determining a geometry plan (e.g., prescribed slices including center, orientation, and extent of anatomical landmark of interest) of a scan (e.g., high resolution scan such as diagnostic scan) of the anatomic landmark of interest of the subject based on the localizer images for one or more of the different anatomical stations (block 230). In certain embodiments, an intelligent prescription module such as AIR$_x$™ from General Electric Healthcare may be utilized in determining the geometry plan. The method 210 yet further includes the initiating the scan (e.g., high resolution or diagnostic scan) to obtain higher solution images of a respective anatomic landmark of interest for one or more of the different anatomical stations (block 232). Higher resolution images (e.g., diagnostic images) have a higher resolution than scout or localizer images as well as calibration images.

Figure 6:
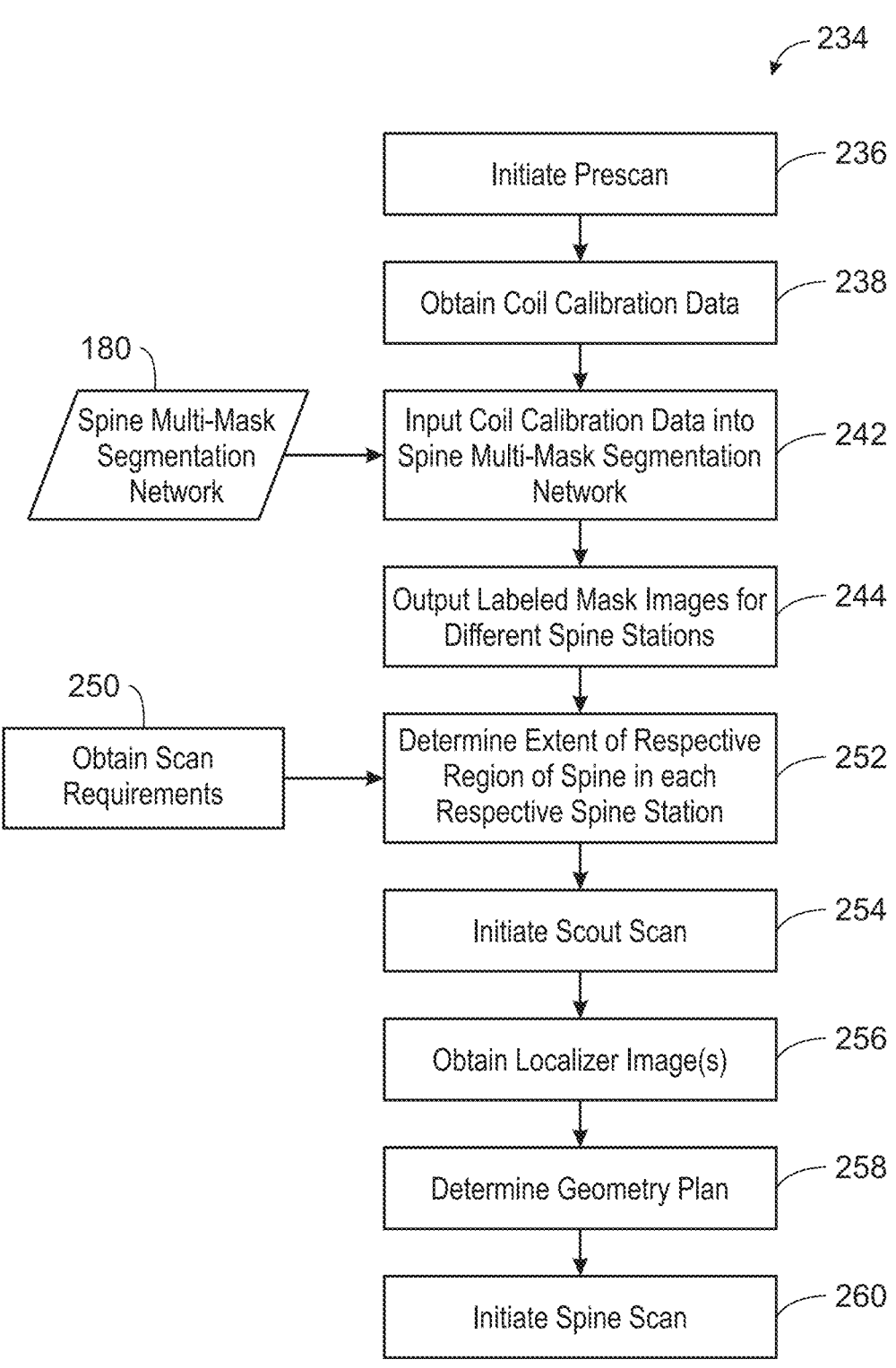
FIG. 6 illustrates a flow diagram of a method for performing a spine scan of a patient utilizing the MRI system in FIG. 1, in accordance with aspects of the present disclosure.

FIG. 6 illustrates a flow diagram of a method 234 for performing a spine scan of a patient utilizing the MRI system in FIG. 1. One or more steps of the method 234 may be performed by processing circuitry of the magnetic resonance imaging system 100 in FIG. 1. One or more of the steps of the method 234 may be performed simultaneously or in a different order from the order depicted in FIG. 6. In certain embodiments, the method 234 may be utilized on low resolution scans (as opposed to calibration scans). In certain embodiments, the method 234 may be utilized on calibration data other than coil calibration data (e.g., ASSET/PURE calibration). In certain embodiments, the calibration data may be obtained from prescan calibration or task calibration.

The method 234 includes initiating a prescan of a subject with an MR scanner (e.g., MR scanner 102) in FIG. 1 (block 236). The prescan include performing a coil calibration scan utilizing one or more coils (e.g., RF surface coil and/or RF body coil).

Figure 7:
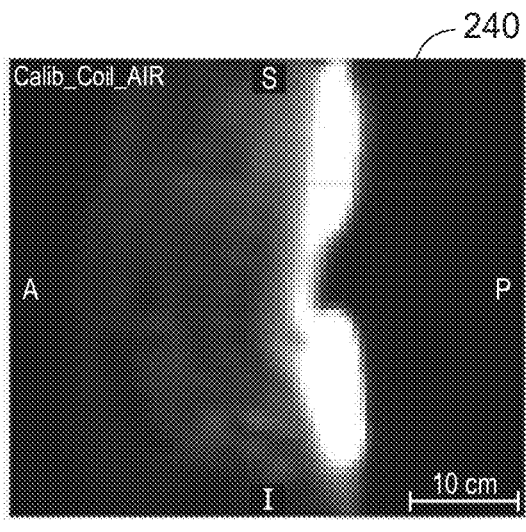
FIG. 7 is an example of coil calibration image of a spine of a subject, in accordance with aspects of the present disclosure.

The method 234 also includes obtaining coil calibration scan data (e.g. coil calibration images) of the subject acquired during the prescan with the MR scanner (block 238). The coil calibration data is large field of view coil calibration data. FIG. 7 is an example of coil calibration image 240 of a spine of a subject. The method 234 further includes inputting the coil calibration data into the trained deep learning-based spine multi-mask segmentation network 180 (block 242). As described above, the deep learning-based spine multi-mask segmentation network 180 is trained for a spine scan. In particular, the deep learning-based spine 180 multi-mask segmentation network is trained to detect and to label the cervical portion of the spine, the thoracic portion of the spine, and the lumbar portion of the spine for the cervical spine station, the thoracic spine station, and the lumbar spine station, respectively. In certain embodiments, the deep learning-based spine multi-mask segmentation network 180 is configured to detect and to label both the cervical and thoracic portion of the spine for a cervico-thoracic spine station, to detect and to label both a thoracic portion and a lumbar portion of a spine for a thoraco-lumbar spine station, and/or to detect and to label an entirety of a spine for a spine station.

Figure 8:
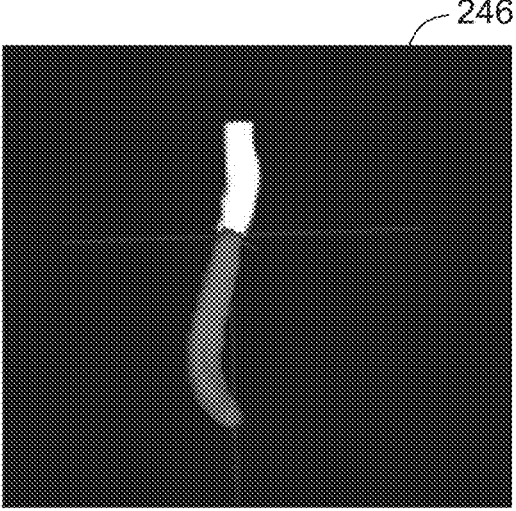
FIG. 8 is an example of an image having masks for a thoracic region and a lumbar region of a spine, in accordance with aspects of the present disclosure.
Figure 9:
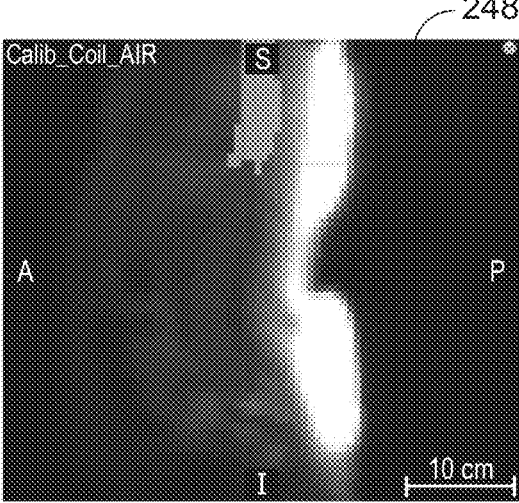
FIG. 9 is an example of an image having the masks for the thoracic region and the lumbar region of the spine in the image in FIG. 8 applied to the coil calibration image of the spine in FIG. 7, in accordance with aspects of the present disclosure.

The method 234 further includes outputting labeled mask images for different spine stations, wherein a respective mask of a respective labeled mask image highlights an particular region of the spine in each respective spine station of the different spine stations (block 244). FIG. 8 is an example of an image 246 having masks for a thoracic region and a lumbar region of a spine. FIG. 9 is an example of an image 248 of the masks for the thoracic region and the lumbar region of the spine in the image 246 in FIG. 8 applied to the coil calibration image 240 of the spine in FIG. 7. The method 234 yet further includes obtaining requirements or information for the spine scan of the subject (block 250). The requirements or information may include a scan protocol, region of interest to be scanned, purpose of the scan, or other information. The requirements or information may be obtained from electronic medical records, radiology information system, and/or other source.

The method 234 even further includes determining (e.g., automatically) an extent (e.g., appropriate field of view (which is superior/inferior based)) of a respective region of a spine in each respective spine station of the different spine stations for a respective localizer scan for each respective spine station based at least on a respective label mask image for each respective spine station (block 252). In certain embodiments, determining the extent of the respective region of a spine in each respective spine station of the different spine stations for the respective localizer scan for each respective spine station based on both the respective label mask image for each respective spine station and the requirements for the scan of the subject. In certain embodiments (when the coil calibration data is obtained from a single RF coil), the extents are determined for the respective region of the spine in each respective spine station of the different spine stations for the single RF coil. In certain embodiments (when the coil calibration data is obtained from multiple RF coils), the extents are determined for the respective region of the spine in each respective spine station of the different spine stations for each of the multiple RF coils.

The method 234 further includes initiating a scout scan (e.g., non-diagnostic scan) of the subject with the MRI system to obtain respective localizer or scout images for one or more of the different spine stations based on the determined extents of the respective regions of the spine (block 254). The localizer images are a series of images (e.g., two-dimensional (2D) images) in the axial, sagittal, and coronal planes (e.g., 3-plane localizer scans). The method 234 even further includes obtaining the localizer images including a respective region of the spine of the subject for one or more of the different spine stations (block 256). The method 234 still further includes determining a geometry plan (e.g., prescribed slices including center, orientation, and extents of region of spine of interest) of a spine scan (e.g., high resolution spine scan such as diagnostic spine scan) of the spine of the subject based on the localizer images for one or more of the different spine stations (block 258). In certain embodiments, an intelligent prescription module such as AIR$_x$™ from General Electric Healthcare may be utilized in determining the geometry plan. The method 234 yet further includes the initiating the spine scan (e.g., high resolution or diagnostic spine scan) to obtain higher solution images of a respective region of the spine for one or more of the different spine stations (block 260). Higher resolution images (e.g., diagnostic images) have a higher resolution than scout or localizer images as well as calibration images.

Figure 10:
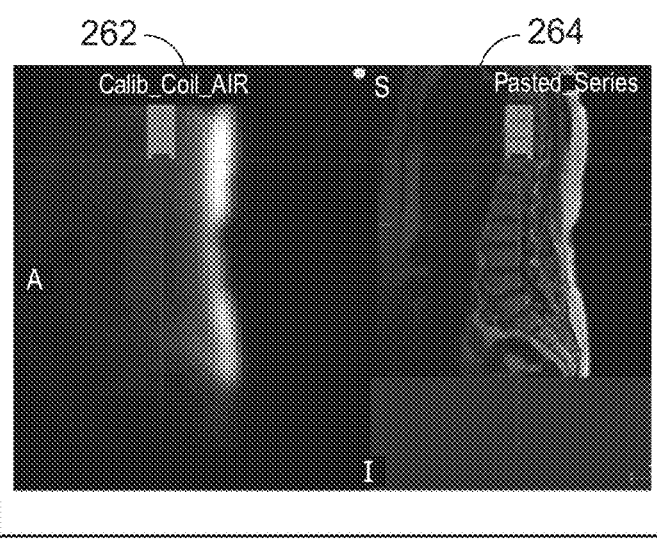
FIG. 10 is an example of a coil calibration image labeled with a mask identifying a thoracic region of the spine along with a corresponding ground truth image, in accordance with aspects of the present disclosure.
Figure 11:
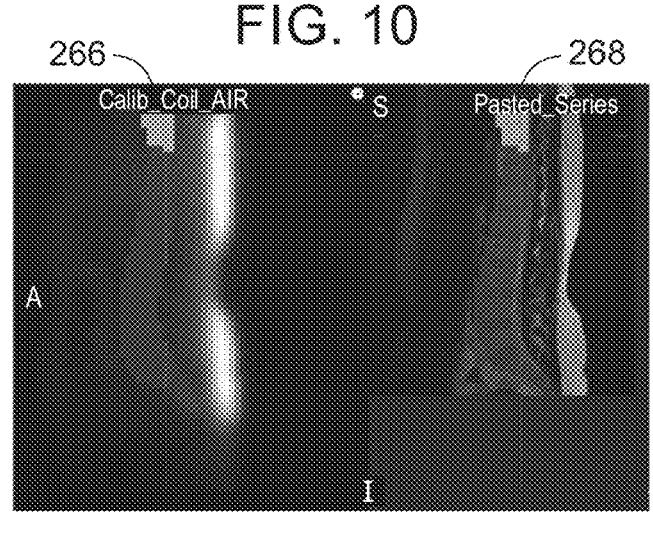
FIG. 11 is another example of a coil calibration image labeled with a mask identifying a thoracic region of the spine along with a corresponding ground truth image, in accordance with aspects of the present disclosure.
Figure 12:
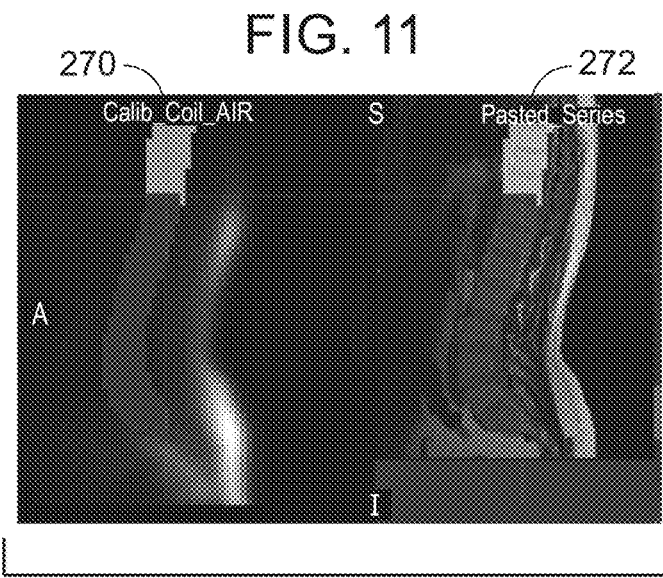
FIG. 12 is a further example of a coil calibration image labeled with a mask identifying a thoracic region of the spine along with a corresponding ground truth image, in accordance with aspects of the present disclosure.

FIG. 10 is an example of a coil calibration image 262 labeled with a mask identifying a thoracic region of the spine along with a corresponding ground truth image 264 utilizing the method 234 in FIG. 9. The ground truth image 264 is a higher resolution image obtained from pasting different images together. FIG. 11 is another example of a coil calibration image 266 labeled with a mask identifying a thoracic region of the spine along with a corresponding ground truth image 268 utilizing the method 234 in FIG. 9. The ground truth image 268 is a higher resolution image obtained from pasting different images together. FIG. 12 is a further example of a coil calibration image 270 labeled with a mask identifying a thoracic region of the spine along with a corresponding ground truth image 272 utilizing the method 234 in FIG. 9. The ground truth image 272 is higher resolution image obtained from pasting different images together.

Figure 13:
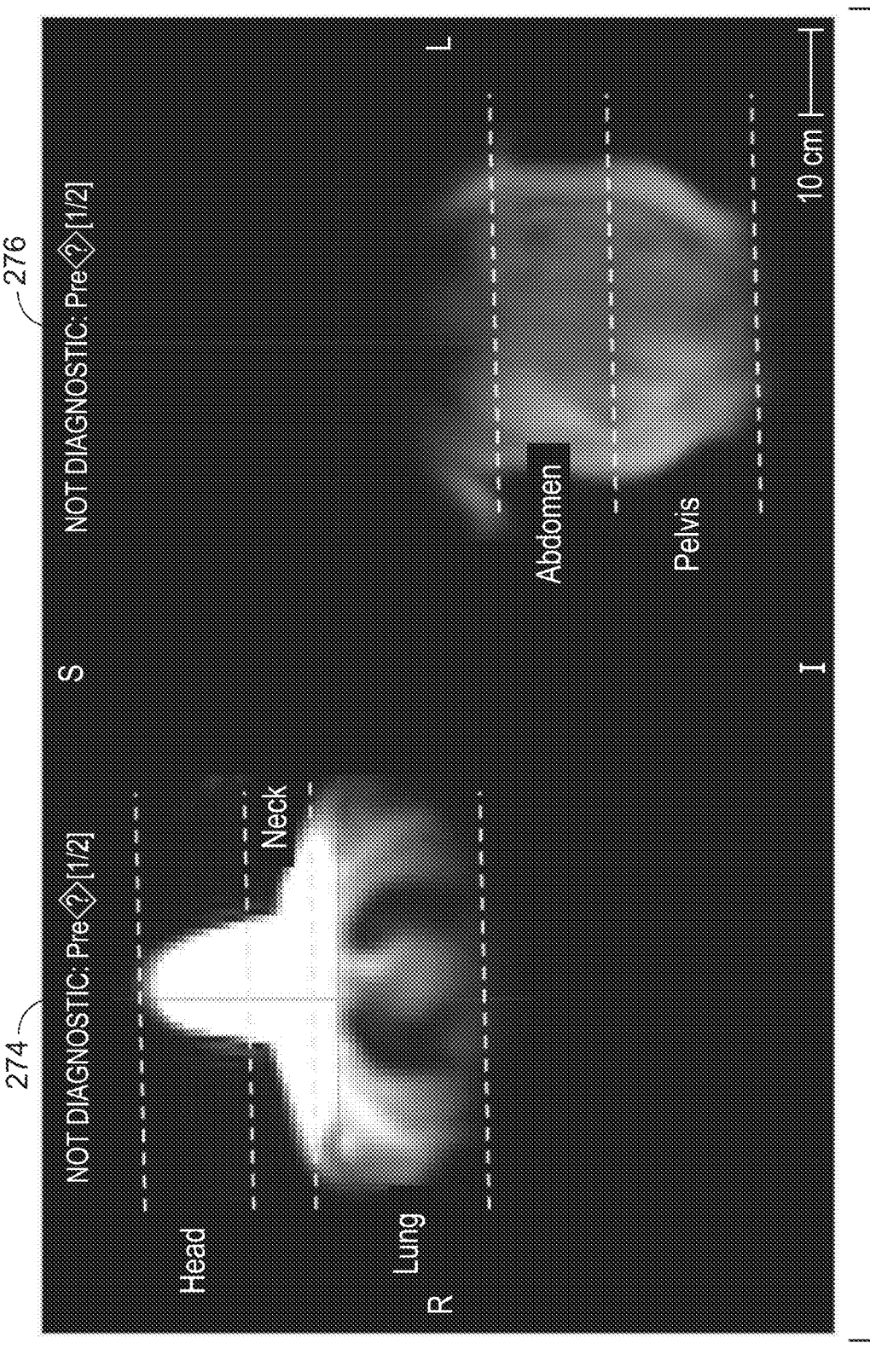
FIG. 13 is an example of coil calibration images of a first portion and a second portion of a body of a subject, in accordance with aspects of the present disclosure.

The techniques described above can be extended to other applications of anatomy parcellation such as station identification in PET/MR MRAC setup or whole body examination setup. FIG. 13 is an example of coil calibration images 274, 276 of a first portion and a second portion of a body of a subject, respectively. As marked, the coil calibration image 274 includes the head, the neck, and the lung. As marked, the coil calibration image 276 includes the abdomen and the pelvis. The method 210 described in FIG. 5 can be utilized to label respective anatomical landmarks of interest within the different anatomical stations (e.g., utilizing the either the whole body multi-mask segmentation network 182 or the PET/MR MRAC multi-mask segmentation network 184 described in FIG. 2), which can then be utilized to determine the extent of each respective anatomical landmark of interest in each of the different anatomical stations. For example, the different anatomical stations may be the head, the thorax, the abdomen, and the pelvis region. The number of anatomical stations may vary depending on the application. In addition, what portion of the body is included in each anatomical station may vary depending on the application.

Similarly, the techniques described above can be extended to other regions of interest of the body for parcellation. For example, the method 210 described in FIG. 5 can be utilized to label respective anatomical landmarks of interest within a particular region of interest (e.g., utilizing the region of interest multi-mask segmentation network 186 described in FIG. 2), which can then be utilized to determine the extent of each respective anatomical landmark of interest in a region of interest. For example, the method 210 described in FIG. 5 could be applied to the lung to detect and to label and to determine the respective extent of different portions of a lung. In another example, the method 210 described in FIG. 5 could be applied to the shoulder to detect and to label and to determine the respective extent of different portion of the shoulder.

Technical effects of the disclosed subject matter include providing for automatic patient specific extent estimation for correct localizer or high resolution scans during a prescan stage. For example, the disclosed embodiments enable techniques to determine a spine station (e.g., cervical, thoracic, lumbar) extent automatically from calibration images as part of a prescan and have the correct station localizer scanned for further usage by the technologist in planning a spine examination. These techniques can be extended to determining other anatomical boundaries in context of a whole body imaging or PET/MR MRAC boundaries. With these techniques, all the presets necessary for region stratification are made available from prescan data and geometrically with geometrically and patient specific localizers made available on the go for the technologist. Technical effects of the disclosed subject matter include ensuring that the correct station (e.g., cervical only or thoracic only or lumbar only) or station (e.g., cervico-throracic, thoraco-lumbar or entire spine) localizers are automatically available to a user for spine planning. This is especially so for the thoracic station, which is typically split across two localizers in current practice. Technical effects of the subject matter also includes allowing for a single localizer to be generated automatically. Technical effects of the subject matter further include removing the need for pasting. Technical effects of the subject matter even further include facilitating easy setup for planning the examination. The disclosed embodiments are also useful for automatically setting up the patient anatomy specific superior/inferior coverage preset for multi-station whole body imaging examination (e.g., PET/MR MRAC). Technical effects of the disclosed subject matter yet further include reducing the time in setting up a subsequent can (e.g., localizer scan and/or higher resolution scan (e.g., diagnostic scan)).

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112 (f). However, for any claims containing elements designated in any other manner, it is intended that such elements are not to be interpreted under 35 U.S.C. 112 (f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for performing region stratification on calibration images, comprising:
   obtaining, at a processor, calibration scan data of a subject acquired with a magnetic resonance (MR) scanner of an MR imaging system, wherein the calibration scan data comprises coil calibration data, and wherein the coil calibration data is obtained from a plurality of radio frequency coils;
   inputting, via the processor, the calibration scan data into a trained deep learning-based multi-mask segmentation network;
   outputting, via the processor, from the trained deep learning-based multi-mask segmentation network labeled mask images for different anatomical stations, wherein a respective mask of a respective labeled mask image highlights an anatomical landmark of interest in a respective anatomical station of the different anatomical stations; and
   determining, via the processor, an extent of a respective anatomical landmark of interest in each respective anatomical station of the different anatomical stations for a respective localizer scan for each respective anatomical station based at least on the respective labeled mask image for each respective anatomical station, wherein the extent of the respective anatomical landmark of interest in each respective anatomical station of the different anatomical stations is determined for each radio frequency coil of the plurality of radio frequency coils for the respective localizer scan for each respective anatomical station.

2. The computer-implemented method of claim 1, wherein the trained deep learning-based multi-mask segmentation network is trained to detect and to label the respective anatomical landmark of interest in each respective anatomical station of the different anatomical stations.

3. The computer-implemented method of claim 1, further comprising obtaining, at the processor, requirements for a scan of the subject.

4. The computer-implemented method of claim 3, wherein determining the extent of the respective anatomical landmark of interest in each respective anatomical station of the different anatomical stations for the respective localizer scan for each respective anatomical station based on both the respective labeled mask image for each respective anatomical station and the requirements for the scan of the subject.

5. The computer-implemented method claim 1, wherein the different anatomical stations are for a spine scan with the MR scanner.

6. The computer-implemented method of claim 1, wherein the different anatomical stations are for a whole body scan with the MR scanner.

7. The computer-implemented method of claim 1, wherein the different anatomical stations are for an MR imaging-based attenuation correction scan with the MR scanner and a positron emission tomography (PET) scanner, wherein the MR imaging system is part of a PET/MR imaging system.

8. A system for performing region stratification on calibration images, comprising:
   a memory encoding processor-executable routines; and
   a processor configured to access the memory and to execute the processor-executable routines, wherein the processor-executable routines, when executed by the processor, cause the processor to:
   obtain calibration scan data of a subject acquired with a magnetic resonance (MR) scanner of an MR imaging system, wherein the calibration scan data comprises coil calibration data, and wherein the coil calibration data is obtained from a plurality of radio frequency coils;
   input the calibration scan data into a trained deep learning-based multi-mask segmentation network;
   output from the trained deep learning-based multi-mask segmentation network labeled mask images for different anatomical stations, wherein a respective mask of a respective labeled mask image highlights an anatomical landmark of interest in a respective anatomical station of the different anatomical stations; and
   determine an extent of a respective anatomical landmark of interest in each respective anatomical station of the different anatomical stations for a respective localizer scan for each respective anatomical station based at least on the respective labeled mask image for each respective anatomical station, wherein the extent of the respective anatomical landmark of interest in each respective anatomical station of the different anatomical stations is determined for each radio frequency coil of the plurality of radio frequency coils for the respective localizer scan for each respective anatomical station.

9. The system of claim 8, wherein the trained deep learning-based multi-mask segmentation network is trained to detect and to label the respective anatomical landmark of interest in each respective anatomical station of the different anatomical stations.

10. The system of claim 8, wherein the processor-executable routines, when executed by the processor, further cause the processor to obtain requirements for a scan of the subject, and wherein determining the extent of the respective anatomical landmark of interest in each respective anatomical station of the different anatomical stations for the respective localizer scan for each respective anatomical station based on both the respective labeled mask image for each respective anatomical station and the requirements for the scan of the subject.

11. The system claim 8, wherein the different anatomical stations are for a spine scan with the MR scanner.

12. The system of claim 8, wherein the different anatomical stations are for a whole body scan with the MR scanner.

13. The system of claim 8, wherein the different anatomical stations are for an MR imaging-based attenuation correction scan with the MR scanner and a positron emission tomography (PET) scanner, wherein the MR imaging system is part of a PET/MR imaging system.

* * * * *